(12) United States Patent
Pahuja et al.

(10) Patent No.: US 9,826,920 B2
(45) Date of Patent: Nov. 28, 2017

(54) DISPOSABLE DUAL TIPPED EAR CURETTE INCORPORATING DEPTH MEASUREMENT SYSTEM

(76) Inventors: Deepak Pahuja, Erie, PA (US); Ryan Scott Bookhamer, Edinboro, PA (US)

( * ) Notice: Subject to any disclaimer, the term of this patent is extended or adjusted under 35 U.S.C. 154(b) by 1245 days.

(21) Appl. No.: 13/480,524

(22) Filed: May 25, 2012

(65) Prior Publication Data

US 2013/0190647 A1 Jul. 25, 2013

Related U.S. Application Data

(60) Provisional application No. 61/632,235, filed on Jan. 20, 2012.

(51) Int. Cl.
| | | |
|---|---|---|
| *A61B 5/107* | (2006.01) | |
| *A61F 11/00* | (2006.01) | |
| *A61B 17/3207* | (2006.01) | |
| *A61B 90/00* | (2016.01) | |

(52) U.S. Cl.
CPC .......... *A61B 5/1076* (2013.01); *A61F 11/006* (2013.01); *A61B 17/320708* (2013.01); *A61B 2090/062* (2016.02)

(58) Field of Classification Search
CPC .................................................... A61F 11/006
See application file for complete search history.

(56) References Cited

U.S. PATENT DOCUMENTS

| | | |
|---|---|---|
| 1,449,165 A | 3/1923 | Cameron |
| 1,533,123 A | 4/1925 | Lewis |
| 1,737,106 A | 11/1926 | Campbell |
| 2,331,732 A | 10/1943 | Ryzmek |
| 2,885,537 A | 5/1959 | Wood |
| 3,195,536 A | 7/1965 | Hovnanian |
| 3,254,356 A | 6/1966 | Kou et al. |
| D219,252 S | 11/1970 | Bogoff |
| 3,592,186 A | 7/1971 | Oster |
| 3,626,946 A | 12/1971 | Messey |
| 3,635,222 A | 1/1972 | Robinson |
| 3,670,732 A | 6/1972 | Robinson |

(Continued)

FOREIGN PATENT DOCUMENTS

| | | | |
|---|---|---|---|
| CN | 201361176 Y | * 12/2009 | |
| FR | 2848814 A3 | * 6/2004 | ............. A61F 11/00 |

OTHER PUBLICATIONS

Machine English Translation of FR 2848814 A3.*

*Primary Examiner* — Matthew Kremer
(74) *Attorney, Agent, or Firm* — Blynn L. Shideler; Krisanne Shideler; BLK Law Group

(57) ABSTRACT

A disposable dual ended ear curette incorporates specialized tip configurations and a depth measurement system. The ear curette may comprise a central handle portion; a first tip extending from one end of the handle portion and including an annular array of projections; and a second tip extending from an opposed end of the handle portion and including a blade member having a first lateral scraping edge on one edge of the blade member positioned adjacent a concave surface of the blade member, and a second lateral scraping edge on an opposed edge of the blade member. The ear curette may further include a sequence of spaced, visible measurement indicia on each tip, configured to provide an operator with a visual indication of the depth of operation of the associated tip in a patient's ear.

17 Claims, 5 Drawing Sheets

(56) References Cited

U.S. PATENT DOCUMENTS

| | | | |
|---|---|---|---|
| 4,027,658 | A | 6/1977 | Marshall |
| 4,044,770 | A | 8/1977 | Ocel et al. |
| 4,411,265 | A | 10/1983 | Eichenlaub |
| D275,127 | S | 8/1984 | Edwards |
| 4,566,439 | A | 1/1986 | Burgin |
| 4,572,180 | A | 2/1986 | Deenadayalu |
| D318,117 | S | 7/1991 | Michelson |
| 5,209,757 | A | 5/1993 | Krug et al. |
| 5,234,452 | A | 8/1993 | Wang-On |
| 5,250,061 | A | 10/1993 | Michelson |
| 5,348,023 | A | 9/1994 | McLucas |
| D368,520 | S | 4/1996 | Brewer, Jr. |
| D372,311 | S | 7/1996 | Koros et al. |
| 5,586,989 | A | 12/1996 | Bray, Jr. |
| 5,632,756 | A | 5/1997 | Kruglick |
| D381,426 | S | 7/1997 | Koros et al. |
| 5,715,850 | A | 2/1998 | Markgraaf |
| D393,312 | S | 4/1998 | Huttner |
| D415,275 | S | 10/1999 | Huttner |
| D420,133 | S | 2/2000 | Huttner |
| D423,669 | S | 4/2000 | Huttner |
| D428,489 | S | 7/2000 | Huttner |
| D439,338 | S | 3/2001 | Huttner |
| D445,503 | S | 7/2001 | Huttner |
| D447,237 | S | 8/2001 | Huttner |
| D449,888 | S | 10/2001 | Huttner |
| D450,676 | S | 11/2001 | Huttner |
| 6,522,912 | B1 * | 2/2003 | Nakatani et al. .............. 600/474 |
| D539,426 | S | 3/2007 | Callaghan |
| 2005/0096678 | A1 * | 5/2005 | Olson ........................... 606/162 |
| 2010/0042122 | A1 | 2/2010 | Shaw, Jr. |
| 2012/0296355 | A1 * | 11/2012 | Burres .................. A61F 11/006 |
| | | | 606/162 |

\* cited by examiner

SOFT AND RIGID BRISTLES CLEAN AND REMOVES OBSTRUCTION FROM EAR CANAL

DUAL END CURETTE: REMOVAL END AND SCRAPING END

MEASUREMENT SYSTEM: DEPTH MEASUREMENTS ON THE CURETTE TOWARD TIP

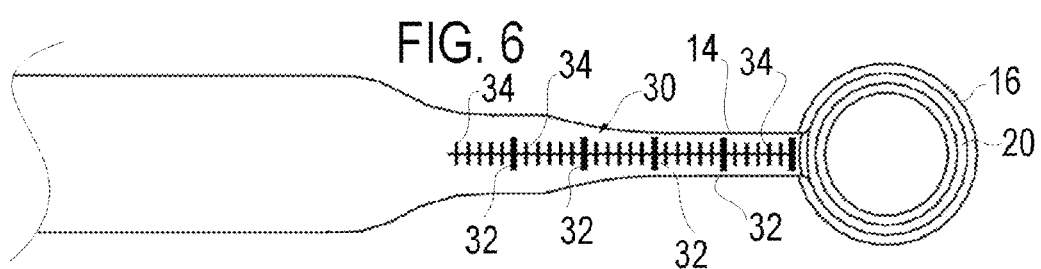
FIG. 6
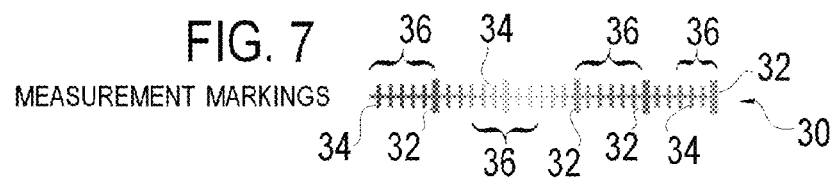
FIG. 7 MEASUREMENT MARKINGS
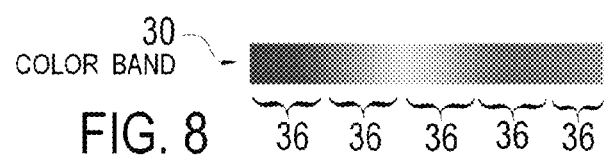
COLOR BAND
FIG. 8

RIDGES TO GRASP MATERIAL
GROOVES ON ENGE OF SCOOP

RIDGES TO GRASP MATERIAL
INTERIOR AND EXTERIOR RIDGES

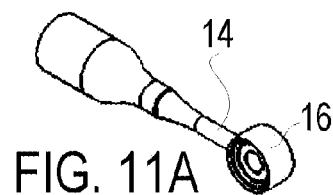
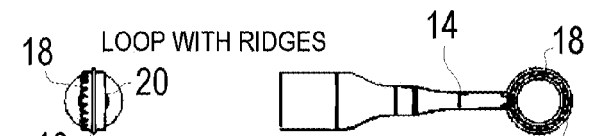
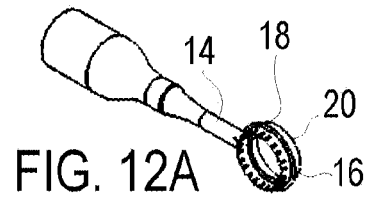
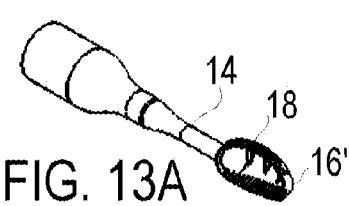
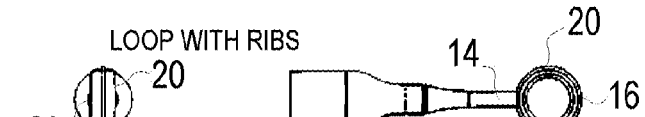
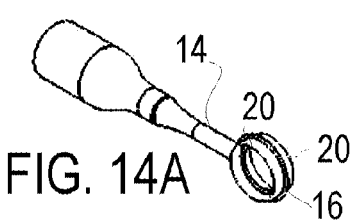
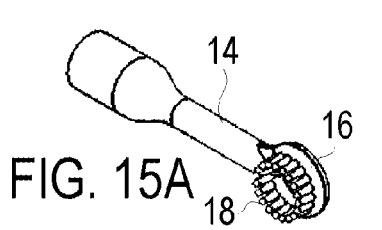

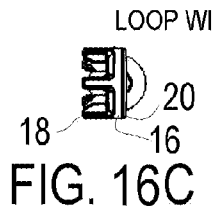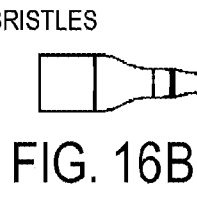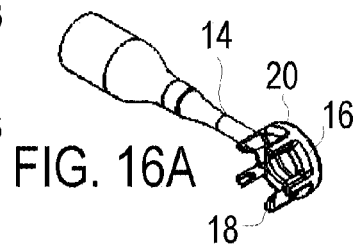
FIG. 16C — LOOP WITH BRISTLES — FIG. 16B — FIG. 16A
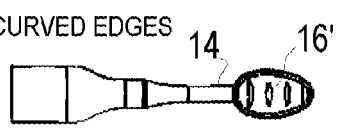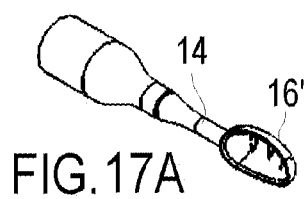
FIG. 17C — SCOOP WITH CURVED EDGES — FIG. 17B — FIG. 17A
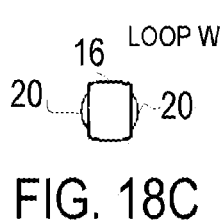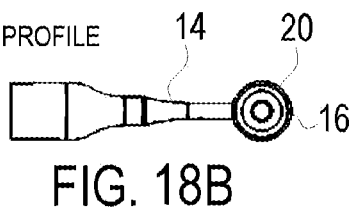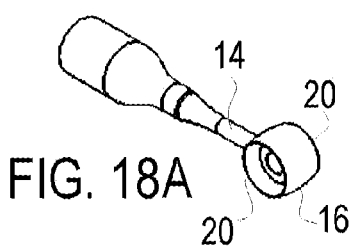
FIG. 18C — LOOP WITH U PROFILE — FIG. 18B — FIG. 18A
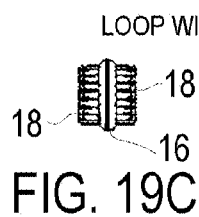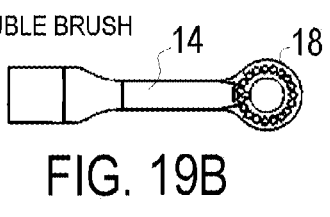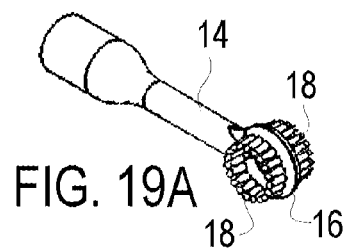
FIG. 19C — LOOP WITH DOUBLE BRUSH — FIG. 19B — FIG. 19A
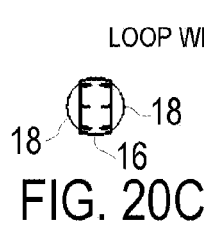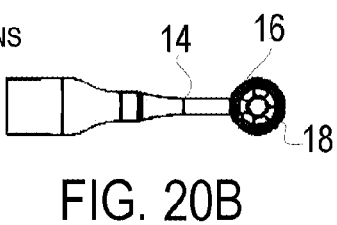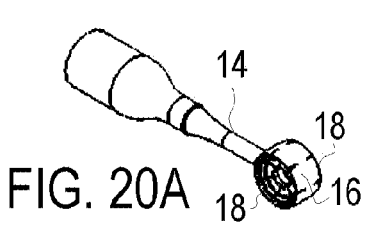
FIG. 20C — LOOP WITH FINS — FIG. 20B — FIG. 20A of the invention

DISPOSABLE DUAL TIPPED EAR CURETTE INCORPORATING DEPTH MEASUREMENT SYSTEM

RELATED APPLICATIONS

This application claims the benefit of U.S. Provisional patent application Ser. No. 61/632,235 filed Jan. 20, 2012.

BACKGROUND OF THE INVENTION

1. Field of the Invention

The present invention relates to ear curettes, more particularly, the present invention relates to disposable ear curettes with specialized tip configurations and incorporating a depth measurement system.

2. Background Information

Cerumen, commonly called ear wax, is produced in the outer third of the cartilaginous portion of the human ear canal. It is a mixture of viscous secretions from sebaceous glands and less-viscous ones from modified apocrine sweat glands. The primary components of cerumen have been identified as comprising shed layers of skin, with 60% of the cerumen consisting of keratin, 12-20% saturated and unsaturated long-chain fatty acids, alcohols, squalene and 6-9% cholesterol.

There are two distinct genetically determined types of cerumen: the wet type, which is dominant, and the dry type, which is recessive. While Asians and Native Americans have been identified as more likely to have the dry type of cerumen (gray and flaky), and Caucasian and Blacks have been listed as being more likely to have the wet type (honey-brown to dark-brown and moist).

The American Academy of Otolaryngology discourages earwax removal unless excess earwax is causing health problems. A number of softeners are effective; however, and another common method of cerumen removal is syringing or irrigation with warm water. Finally, a curette based method is often used by otolaryngologists when the ear canal is partially occluded and the material is not adhering to the skin of the ear canal.

Cerumen removal utilizing an ear curette has been estimated to be performed approximately 22 million times annually with the number expected to grow as the baby boomer generation ages.

Numerous ear curette designs have been proposed over the years.

Although not an ear curette per se, a 1975 development shown in U.S. Pat. No. 4,027,658 shows a sample taking instrument comprising handle portion and an operative tip extending from one end of the handle portion with the tip including an elongated cylindrical end with longitudinal and circumferential grooves therein.

A 1981 design is shown in U.S. Pat. No. D275,127 and comprises a polygonal in cross-section handle portion (which prevents instrument rolling on an instrument tray) and an operative tip extending from one end of the handle portion with the tip including an annular open circular scraping ring.

A 1988 design is shown in U.S. Pat. No. D318,117 and comprises a distal handle portion and an operative tip extending from one end of the handle portion with the tip including an annular open circular scraping ring.

A 1992 design is shown in U.S. Pat. No. 5,348,023 and comprises a distal handle portion and an operative tip extending from one end of the handle portion with the tip including a closed spoon type scraping member.

A 1994 design is shown in U.S. Pat. No. D368,520 and comprises a central handle portion and a first operative tip extending from one end of the handle portion with the first tip including an open circular shaped scraping member extending along the axis of the handle and having opposed scraping surfaces of distinct diameters. A second opposed end includes a ball with no known curette function.

A 1994 design is shown in U.S. Pat. No. 5,632,756 and comprises a handle portion and an operative tip extending from one end of the handle portion with the tip including a "bulbous banded cage" scraping member.

A 1995 design is shown in U.S. Pat. No. D372,311 and comprises a handle portion and an operative tip extending from one end of the handle portion with the tip including an annular closed oval scraping ring and the device further including a suction or irrigation tube extending to the scraping ring.

A 1995 design is shown in U.S. Pat. No. D381,426 and comprises a handle portion and an operative tip extending from one end of the handle portion with the tip including an annular closed oval scraping ring extending at an oblique angle relative to the handle.

A 1995 design is shown in U.S. Pat. No. 5,586,989 and comprises a handle portion with an offset and an operative tip extending from the offset end of the handle portion with the tip including an annular closed oval scraping ring extending at an oblique angle relative to the tip and handle.

A 1996 design is shown in U.S. Pat. No. 5,715,850 and comprises a handle portion with an operative tip extending from the end of the handle portion with the tip including one of a series of scraping members at an end thereof. The scraping members disclosed include a series of wire looped designs of FIGS. 2 and 3a, 3b and 3c, a wire spiral design of FIG. 3d, and four longitudinally extending radial scraping edges in FIG. 3e.

A 1997 design is shown in U.S. Pat. No. D393,312 and comprises a handle portion and an operative tip extending from one end of the handle portion with the tip including an open oval shaped scraping member extending along the axis of the handle.

Two 1997 designs shown in U.S. Pat. Nos. D415,275 and D420,133 each comprises a handle portion and an operative tip extending from one end of the handle portion with the tip including an closed spoon type scraping member extending along the axis of the handle.

A 1998 design is shown in U.S. Pat. No. D428,489 and comprises a handle portion and an operative tip extending from one end of the handle portion with the tip including an open circular shaped scraping member extending at an oblique angle relative to the axis of the handle.

A 1998 design is shown in U.S. Pat. No. D445,503 and comprises a handle portion and an operative tip extending from one end of the handle portion with the tip including an open expanding oval or tear-dropped shaped scraping member extending along the axis of the handle.

A 1999 design is shown in U.S. Pat. No. D423,669 and comprises a central handle portion and a first operative tip extending from one end of the handle portion with the first tip including an open circular shaped scraping member extending along the axis of the handle, and a second operative tip extending from an opposed end of the handle portion with the second tip including a closed spoon type scraping member.

A 1999 design is shown in U.S. Pat. No. D439,338 and comprises a handle portion and an operative tip extending from one end of the handle portion with the tip including an open tear-dropped shaped scraping member extending along the axis of the handle.

A 2001 design is shown in U.S. Pat. No. D449,888 and comprises a handle portion and an operative tip extending from one end of the handle portion with the tip including an open trapezoidal shaped scraping member curving away from the axis of the handle.

A 2001 design is shown in U.S. Pat. No. D450,676 and comprises a handle portion and an operative tip extending from one end of the handle portion with the tip including an open trapezoidal shaped scraping member curving away from the axis of the handle.

A 2005 design is shown in U.S. Pat. No. D539,426 and comprises an ergonomic central handle portion configured for a pair of operative tips extending from each end of the handle portion with each tip including an open circular shaped scraping member extending at an angle relative to the axis of the handle.

A 2009 design is shown in U.S. Published Patent Application No. 2010-0042122 and comprises a central triangular handle portion configured for a pair of operative tips extending from each end of the handle portion with each tip including an open circular shaped scraping member extending at an angle relative to the axis of the handle, or solid trapezoidal shaped scraping members.

The above mentioned patents and published patent applications are incorporated herein by reference and provide an overview of the ear curette art. The above prior art designs fails to provide an ear curette tool that is easily accommodated to removal of the two distinct types of cerumen, i.e. the wet type and the dry type. If the ear curette utilized by the professional in the cerumen removal is not adequate for the type of cerumen encountered then there is an increased likelihood of additional trauma to the patient, increase in the length of the procedure, increase in the technical difficulty in performing the procedure by the health care professional, and an increase in the likelihood of subsequent procedures (e.g., softeners with extended or repeated irrigation).

Additionally the administration of health care is increasing the issues encountered with this cerumen removal medical procedure. For example some medical billing codes will distinguish between an instrument based cerumen removal such as with a curette (for cerumen which is considered clinically "impacted" this is classified as a surgical procedure) and a non-instrument based cerumen removal process such as a lavage that may be performed by a nurse. This distinction in classification and whether or not it is a surgical procedure has resulted in a demand for greater documentation of the surgical procedure, such as detailing the reasons for impaction. This move to greater documentation for the surgical curette based procedures is now including a description of the depth within the ear of the impacted cerumen being removed.

There is no current system for health care professionals in a cerumen removal for easily objectively quantifying the depth within the ear of the impacted cerumen being removed. Without such system the health care professionals will merely estimate the depth within the ear of the impacted cerumen being removed resulting in non-objective and non-verifiable documentation.

It is an object of the present invention to minimize the drawbacks of the existing ear curettes and to provide a simple, cost effective, efficient and safe ear curette that can be utilized for both types of cerumen and which provide a depth measurement system for objective measurement by the users.

SUMMARY OF THE INVENTION

The various embodiments and examples of the present invention as presented herein are understood to be illustrative of the present invention and not restrictive thereof and are non-limiting with respect to the scope of the invention.

At least some of the above stated objects are achieved with an ear curette comprising a central handle portion; a first tip extending from one end of the handle portion and including an annular array of projections; and a second tip extending from an opposed end of the handle portion and including a blade member having a first lateral scraping edge on one edge of the blade member positioned adjacent a concave surface of the blade member, and a second lateral scraping edge on an opposed edge of the blade member.

At least some of the objects of the invention are achieved with an ear curette comprising a handle portion and a tip extending from one end of the handle portion and including an annular array of projections.

At least some of the objects of the invention are achieved with an ear curette comprising a handle portion and at least one operative tip extending from one end of the handle portion and including a sequence of spaced, visible measurement indicia on each tip, configured to provide an operator with a visual indication of the depth of operation of the associated tip in a patient's ear wherein the spaced, visible measurement indicia includes at least one of i) evenly spaced unit gradation indicia and evenly spaced subunit gradations between the unit gradation indicia, ii) alphanumerical indicia indicative of the depth of operation of the associated tip in a patient's ear, and iii) a spectrum of colors that varies in accordance with the depth of operation of the associated tip in a patient's ear.

At least some of the objects of the invention are achieved with an ear curette comprising a handle portion and a tip extending from one end of the handle portion and including a blade member having a first lateral scraping edge on one edge of the blade member positioned adjacent a concave surface of the blade member, and a second lateral scraping edge on an opposed edge of the blade member wherein the blade member is formed as an S shape in cross section extending between the two scraping edges.

In some embodiments of the present invention one tip of the ear curette includes a ring member extending along plane and wherein the annular array of projections extend from the ring member substantially perpendicular to the plane. The annular array of projections may extend from one side of the ring member and wherein each projection may be formed of one of i) an arc segment projection generally conforming to the radii of the portion of the ring member from which it extends, ii) a frusto-conical member; and iii) having a cross section extending in a general radial direction relative to the ring member. Further, a side of ring member opposed from the annular array of projections may further include an annular scraping edge.

These and other advantages of the present invention will be clarified in the brief description of the preferred embodiment taken together with the drawings in which like reference numerals represent like elements throughout.

BRIEF DESCRIPTION OF THE DRAWINGS

FIG. 6 is an enlarged top plan view of one operative tip of the ear curette incorporating a depth measurement system according FIGS. 1-2;

FIGS. 7 and 8 are enlarged top plan views of alternative depth measurement system marking indicia according alternative embodiments of the present invention;

FIGS. 11a-c to 20a-c are each collected series including a perspective view, top plan view and an end view of each of ten distinct alternative operative tips of the ear curette according to the present invention.

DESCRIPTION OF THE PREFERRED EMBODIMENTS

Figure 1:
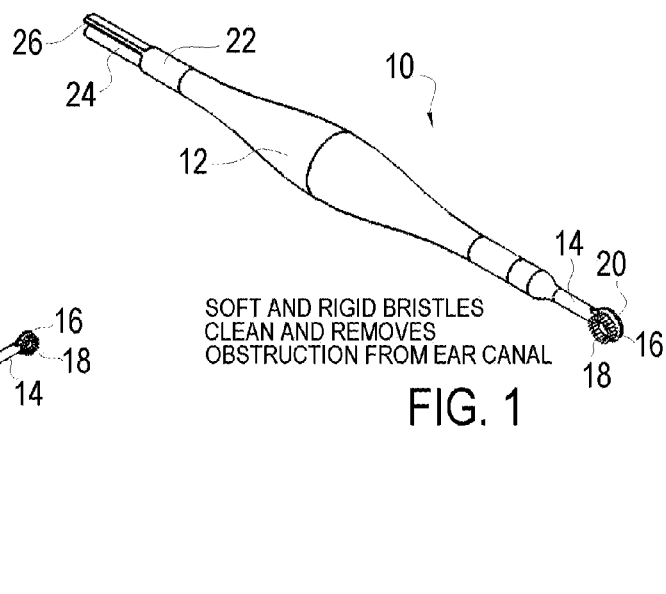
FIGS. 1 and 2 are perspective views of a disposable dual tipped ear curette incorporating a depth measurement system according to a first embodiment of the present invention.
Figure 2:
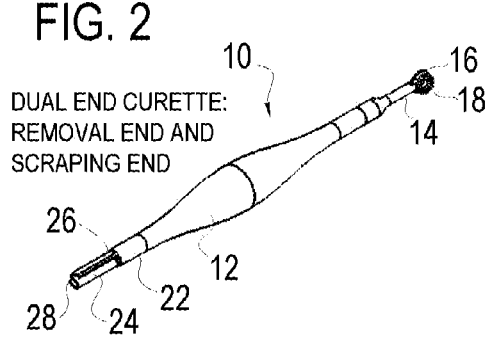
Figure 3:
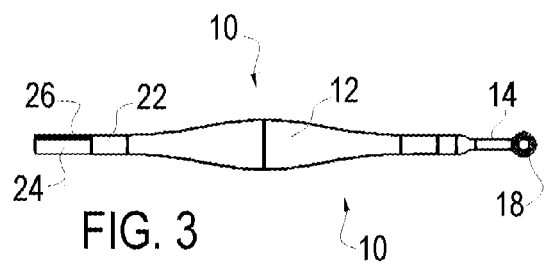
FIG. 3 is a top plan view of the disposable dual tipped ear curette incorporating a depth measurement system according FIGS. 1-2.
Figure 4:
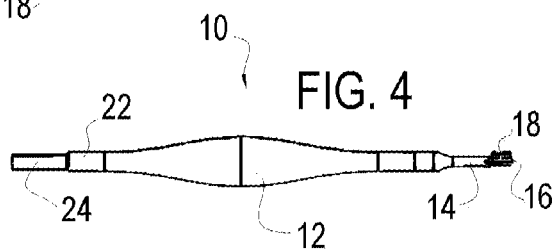
FIG. 4 is an elevation side view of the disposable dual tipped ear curette incorporating a depth measurement system according FIGS. 1-2.
Figure 5:
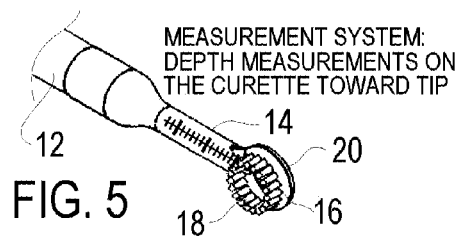
FIG. 5 is an enlarged perspective view of one operative tip of the ear curette incorporating a depth measurement system according FIGS. 1-2.

FIGS. 1 and 2 are perspective views of a disposable dual tipped ear curette 10 incorporating a depth measurement system 30 according to a first embodiment of the present invention. The curette 10 includes a central handle portion 12 formed of smooth flexible polypropylene for ease of manufacture and secure gripping. The handle 12 provides a desired location of the placement of a logo for branding of the curette 10. The shape of the handle 12 can be of any ergonomic design or other utilitarian construction such as including flat surfaces to prevent unwanted rolling of the curette 10 on the instrument tray. The curette 10 is preferably a one piece injection molded construction to keep the costs of manufacture to a minimum and to allow for disposal of the device. Co-injection molding techniques can be used to provide, for example, a softer outer coating to the handle 12 for better tactile qualities for the curette 10.

The curette 10 includes a first tip 14 extending from one end of the handle portion 12. The distal end of the first tip 14 includes an annular generally circular ring member 16 extending along plane and an annular array of projections 18 extending from one side of the ring member 16 substantially perpendicular to the plane of the ring member 16. Each projection 18 in the embodiment shown in FIGS. 1-6 is formed as a frusto-conical member. Other shapes for projections 18 are possible other than those expressly shown herein that may be sufficiently effective such as tubule-spherical shaped projections 18. In the embodiment shown in FIGS. 1-6 a side of ring member 16 opposed from the annular array of projections 18 includes an annular scraping edge 20.

The curette 10 includes a second tip 22 extending from an opposed end of the handle portion 12 and including a blade member 24 having a first lateral scraping edge 26 on one edge of the blade member 24 or surface positioned adjacent a concave surface of the blade member 24, and a second lateral scraping edge 28 on an opposed edge of the blade member 24. The blade member 24 is formed as an S shape in cross section extending between the two scraping edges 28 and 26.

In the blade member 24 the semi spherical S shaped stiff but flexible surface is used to effectively wipe cerumen from the ear canal, wherein the diameter is slight wider than the diameter of the stem 22. The curette 10 is turned or rotated to wipe the walls of the ear canal and the blade member 24 shears way excess wax from canal.

The ear curette 10 of the present invention includes a depth measuring system 30 formed by a sequence of spaced, visible measurement indicia 32, 34, and/or 36 on each tip 14 and 22, configured to provide an operator with an objective, verifiable visual indication of the depth of operation of the associated tip 14 or 22 in a patient's ear. The depth measuring system 30 of curette 10 is best shown in FIGS. 6-8. As shown in FIGS. 6 and 7, the depth measuring system 30 includes evenly spaced unit gradation indicia 32 representing a standard unit of measure such as a centimeter or millimeter or ¼ inch or the like. Further as shown in FIGS. 6 and 7, the depth measuring system 30 includes evenly spaced subunit gradations 32 between the unit gradation indicia 34, and the subunits graduations can represent any desired sub unit such as 0.2 millimeters. The first gradation indicia 32 is preferably at the edge of the ring member 16, and as the ring member 16 has a known length the system 30 gives the user an objective, verifiable, quantifiable measurement of the depth of use of the curette 10 allowing for effective and consistent documentation of procedures from case to case.

As shown in FIGS. 7 and 8 the sequence of spaced, visible measurement indicia forming the system 30 may include a spectrum of colors that varies in bands 34 in accordance with the depth of operation of the associated tip 14 or 22 in a patient's ear. The spectrum or bands 34 of colors includes the color red at substantially the deepest depth of operation of the associated tip 14 or 22 in a patient's ear to give some additional warning or feedback to the operator. As shown in FIG. 6 the spectrum or bands 34 of colors can be implemented with the evenly spaced unit gradation indicia 32 and subunit graduations 34. Alternatively the spectrum or bands 34 of colors can be implemented by themselves as the bands 34 will provide the operator with the visual measurement guide to the depth of operation of the curette 10. It is further anticipated that the system 30 may further include alpha-numerical indicia indicative of the depth of operation of the associated tip in a patient's ear. Alpha-numeric indicia can be used with the bands 34, the gradations 32 and 34 in various combinations. Many variations on the marking measurement system 30 is possible including international measurements on one edge of system 30 and United States standard marking on an opposed sides. Uneven spacing may be utilized to conform to the most standard depth locations encountered in typical procedures.

Figure 9:
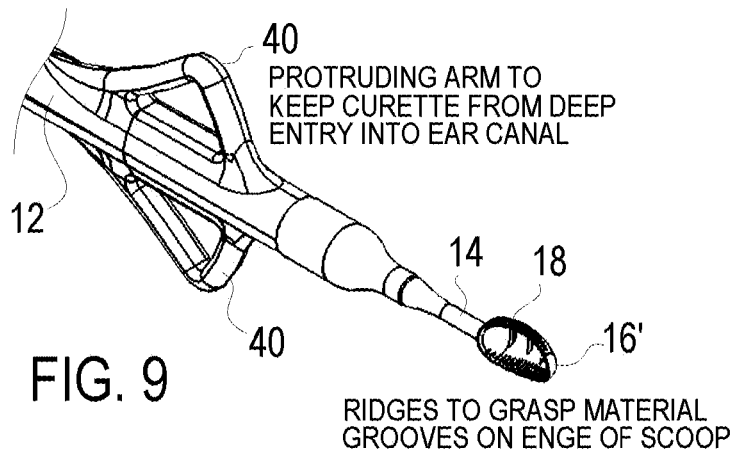
FIG. 9 is a perspective view of an alternative operative tip of the ear curette according to the present invention and incorporating a depth limiting mechanism.

FIG. 9 is a perspective view of an alternative operative tip 14 of the ear curette 10 according to the present invention. In this embodiment the tip 14 has the ring member 16 replaced with a closed spoon type member 16' and the projections 18 are in the form of an oval annular array. The embodiment of FIG. 9 further illustrates the inclusion of a depth limiting mechanism 40 coupled to the handle 12 that prevents the operator from advancing the curette 10 too far within the patient's ear canal. The mechanism can be used with any tip design as desired.

Figure 10:
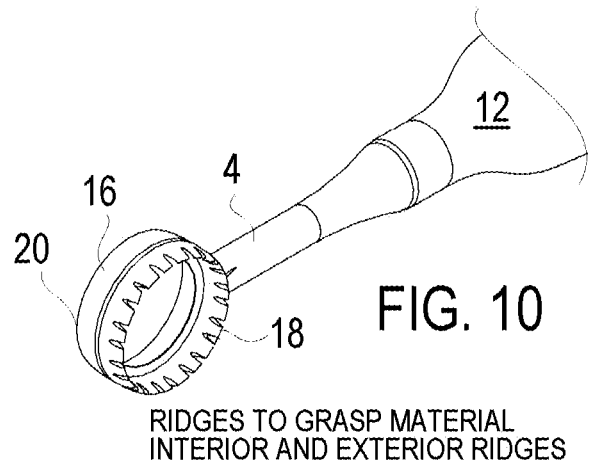
FIG. 10 is a perspective view of an alternative operative tip of the ear curette according to the present invention.

FIG. 10 is a perspective view of an alternative operative tip 14 of the ear curette 10 according to the present invention. The tip 14 includes the ring member 16 and projections 18 and scraping edge 20 similar to that discussed above. In this embodiment the projections 18 are formed of an arc segment projection generally conforming to the radii of the portion of the ring member 16 from which the projection 18 extends.

FIGS. 11a-c to 20a-c are each collected series including a perspective view, top plan view and an end view of each of ten distinct alternative operative tips 14 of the ear curette 10 according to the present invention.

In FIGS. 11a-c, the tip 14 as shown is a loop or ring 16 with interior slots.

In FIGS. 12a-c, the tip 14 as shown is a loop or ring 16 with projections 18 on one side and a scraping edge 20 on an opposed side similar to FIG. 10 discussed above, referred to as a loop with ridges.

In FIGS. 13a-c, the tip 14 as shown is a spoon type closed member or scoop member 16' with projections 18 on one side similar to FIG. 9 discussed above, which may be referred to as a scoop with bristles.

In FIGS. 14a-c, the tip 14 as shown is a ring member 16 with scraping edges 20 on an opposed sides, which may be referred to as a loop with ribs.

In FIGS. 15a-c, the tip 14 as shown is a loop or ring member 16 with frusto-conical projections 18 on one side and a scraping edge 20 on an opposed side, referred to as a loop brush.

In FIGS. 16a-c, the tip 14 as shown is a loop or ring member 16 with projections 18 on one side and a scraping edge 20 on an opposed side, referred to as a loop with bristles. As shown each projection 18 includes a cross section extending in a general radial direction relative to the ring member 16.

In FIGS. 17a-c, the tip 14 as shown is a spoon or scoop member 16', referred to as scoop with curved edges.

In FIGS. 18a-c, the tip 14 as shown is a loop or ring member 16 with scraping edges 20 on opposed sides, referred to as a loop with U-profile.

In FIGS. 19a-c, the tip 14 as shown is a loop or ring member 16 with an annular array of frusto-conical projections 18 on both sides of member 16, referred to as a double brush.

In FIGS. 20a-c, the tip 14 as shown is a loop or ring member 16 with an annular array of frusto-conical projections 18 on both sides of member 16, referred to as a loop with fins. Here each projection 18, like FIG. 10, is formed of an arc segment projection generally conforming to the radii of the portion of the ring member 16 from which the projection 18 extends.

As discussed above and illustrated in the figures, this ear curette 10 designed to assist health care professionals in the removal of cerumen or ear wax. The curette features a depth measuring or marking system 30 to assist doctors in determining curette insertion. The curette 10 has various designs of handles and tips 14 and 22 that can be implemented. Preferably the curette 10 is a one piece dual tipped configuration, such as shown in FIGS. 1-5. Further the angular provisions at both ends of the curette 10 allow for manual bending of the front end of curette 10 as desired by the user to reach the ear canal of the patient.

As noted, preferably the ear curettes 10 are made of smooth, flexible polypropylene via injection molding or the like. With this material the curette 10 as shown is Designed to flex and bend when they encounter an obstacle, reducing and avoiding injury to the ear canal or tympanic membrane. The polypropelene, or similar plastic material curette 10, is safer and more comfortable to the patients than stainless steel ear curettes. A further aspect of the invention can be to provide different color coded ear curettes 10, each with specific tips 14 or 22 and designed for a specific type of patient and cerument condition. Further the color coded curettes 10 may be provided in adult and youth sizes. The plastic curette 10 is designed for effective single use such that no sterilization cost or hassles or cross contamination due to insufficient sterilization.

Although the present invention has been described with particularity herein, the scope of the present invention is not limited to the specific embodiment disclosed. It will be apparent to those of ordinary skill in the art that various modifications may be made to the present invention without departing from the spirit and scope thereof. The scope of the present invention is defined in the appended claims and equivalents thereto.

What is claimed is:

1. An ear curette comprising:
a central handle portion;
a first tip extending from one end of the handle portion and including a base having a surface the outer periphery of which is directly coupled to the handle portion and an annular array of at least three projections extending from the base wherein a proximal end of each projection extends from a common base plane on the surface of the base, and wherein a shape of the array conforms to a shape of at least a portion of the outer periphery of the base; and
a second tip extending from an opposed end of the handle portion and including a blade member having a first lateral scraping edge on one edge of the blade member positioned adjacent a concave surface of the blade member, and a second lateral scraping edge on an opposed edge of the blade member.

2. The ear curette of claim 1 wherein the first tip includes having the base formed as a ring member extending along the common base plane and wherein the array of projections extends from the ring member substantially perpendicular to the common base plane.

3. The ear curette of claim 2 wherein the array of projections extend from one side of the ring member, and wherein a side of the ring member opposed from the array of projections includes an annular scraping edge.

4. The ear curette of claim 2 wherein the array of projections extend from one side of the ring member and wherein each projection is formed of one of i) an arc segment projection generally conforming to a radii of a portion of the ring member from which the arc segment projection extends, and ii) a frusto-conical member.

5. The ear curette of claim 4 wherein at least one tip further includes a sequence of spaced, visible measurement indicia configured to provide an operator with a visual indication of a depth of operation of the associated tip in a patient's ear wherein the spaced, visible measurement indicia includes at least one of i) evenly spaced unit gradation indicia and evenly spaced subunit gradations between the unit gradation indicia, ii) alpha-numerical indicia indicative of the depth of operation of the associated tip in the patient's ear, and iii) a spectrum of colors that varies in accordance with the depth of operation of the associated tip in the patient's ear.

6. The ear curette of claim 1 further including a sequence of spaced, visible measurement indicia on at least one tip, configured to provide an operator with a visual indication of a depth of operation of the associated tip in a patient's ear.

7. The ear curette of claim 6 wherein the sequence of spaced, visible measurement indicia includes at least one of i) evenly spaced unit gradation indicia and evenly spaced subunit gradations between the unit gradation indicia, ii) a spectrum of colors that varies in accordance with the depth of operation of the associated tip in the patient's ear, and iii) alpha-numerical indicia indicative of the depth of operation of the associated tip in the patient's ear.

8. The ear curette of claim 7 wherein the sequence of spaced, visible measurement indicia includes the spectrum of colors and wherein the spectrum of colors includes the color red at substantially the deepest depth of operation of the associated tip in the patient's ear.

9. The ear curette of claim 1 wherein the blade member is formed as an S shape in cross section extending between the two scraping edges.

10. An ear curette comprising a handle portion and a tip extending from each end of the handle portion and including at one end a base having a surface an outer periphery of which is directly coupled to the handle portion and an annular array of projections extending from the base wherein a proximal end of each projection extends from a common base plane on the surface of the base, and at an opposed end of the handle portion a blade member having a first lateral scraping edge on one edge of the blade member positioned adjacent a concave surface of the blade member, and a second lateral scraping edge on an opposed edge of the blade member wherein the blade member is formed as an S shape in cross section extending between the two scraping edges.

11. The ear curette of claim 10 wherein the base is formed as a ring member extending along the common base plane and wherein the array of projections extend from the ring member substantially perpendicular to the common base plane, wherein the array of projections extend from one side of the ring member and wherein each projection is formed of one of i) an arc segment projection generally conforming to a radii of a portion of the ring member from which the arc segment projection extends, and ii) a frusto-conical member.

12. The ear curette of claim 11 wherein a side of the ring member opposed from the array of projections includes an annular scraping edge.

13. The ear curette of claim 10 further including a sequence of spaced, visible measurement indicia on at least one tip, configured to provide an operator with a visual indication of a depth of operation of the associated tip in a patient's ear, wherein the spaced, visible measurement indicia includes at least one of i) evenly spaced unit gradation indicia and evenly spaced subunit gradations between the unit gradation indicia, ii) alpha-numerical indicia indicative of the depth of operation of the associated tip in the patient's ear, and iii) a spectrum of colors that varies in accordance with the depth of operation of the associated tip in the patient's ear.

14. The ear curette of claim 13 wherein the spectrum of colors includes the color red at substantially the deepest depth of operation of the associated tip in the patient's ear.

15. An ear curette comprising
a handle portion and
at least one operative tip extending from one end of the handle portion and including a sequence of spaced, visible measurement indicia on the at least one tip, configured to provide an operator with a visual indication of a depth of operation of the associated tip in a patient's ear wherein the spaced, visible measurement indicia includes at least one of i) evenly spaced unit gradation indicia and evenly spaced subunit gradations between the unit gradation indicia, ii) alpha-numerical indicia indicative of the depth of operation of the associated tip in the patient's ear, and iii) a spectrum of colors that varies in accordance with the depth of operation of the associated tip in the patient's ear,
wherein the at least one tip includes a ring member extending along a plane and an annular array of projections extending from the ring member substantially perpendicular to the plane of the ring member, an outer periphery of ring member is directly coupled to the handle portion.

16. The ear curette of claim 15 wherein the spectrum of colors includes the color red at substantially the deepest depth of operation of the associated tip in the patient's ear.

17. The ear curette of claim 15 further including a second tip which includes an S shape blade member having a first lateral scraping edge on one edge of the blade member positioned adjacent a concave surface of the blade member, and a second lateral scraping edge on an opposed edge of the blade member.

* * * * *